(12) United States Patent
Kimura et al.

(10) Patent No.: US 7,326,900 B2
(45) Date of Patent: Feb. 5, 2008

(54) TWO-DIMENSIONAL WEAK RADIATION DETECTOR WITH A DETECTION MEANS BASED ON ORTHOGONAL MODULATION

(75) Inventors: Noriaki Kimura, Tamano (JP); Takayoshi Yumii, Tamano (JP)

(73) Assignee: Mitsui Engineering & Shipbuilding Co., Ltd., Tokyo (JP)

(*) Notice: Subject to any disclaimer, the term of this patent is extended or adjusted under 35 U.S.C. 154(b) by 17 days.

(21) Appl. No.: 10/533,469

(22) PCT Filed: Nov. 18, 2002

(86) PCT No.: PCT/JP02/12022

§ 371 (c)(1),
(2), (4) Date: Jun. 2, 2005

(87) PCT Pub. No.: WO2004/046698

PCT Pub. Date: Jun. 3, 2004

(65) Prior Publication Data

US 2006/0043307 A1    Mar. 2, 2006

(51) Int. Cl.
*H01J 40/14* (2006.01)
(52) U.S. Cl. .................... 250/207; 250/370.01
(58) Field of Classification Search ............. 250/207, 250/370.1
See application file for complete search history.

(56) References Cited

U.S. PATENT DOCUMENTS

| 4,797,944 A | * | 1/1989 | Tanaka | 382/246 |
|---|---|---|---|---|
| 4,805,030 A | * | 2/1989 | Tanaka | 358/426.14 |
| 5,923,036 A | * | 7/1999 | Tague et al. | 250/339.07 |
| 6,492,657 B1 | * | 12/2002 | Burlefinger et al. | 257/10 |
| 6,611,494 B1 | * | 8/2003 | Ovalekar et al. | 370/208 |
| 6,671,411 B1 | * | 12/2003 | Satoh | 382/239 |
| 2002/0085261 A1 | * | 7/2002 | Makino | 359/196 |
| 2007/0051893 A1 | * | 3/2007 | Matsumoto | 250/370.01 |

FOREIGN PATENT DOCUMENTS

| JP | A 7-50149 | 2/1995 |
|---|---|---|
| JP | A 2001-108684 | 4/2001 |
| JP | A 2002-203508 | 7/2002 |

* cited by examiner

*Primary Examiner*—Georgia Epps
*Assistant Examiner*—Kevin Wyatt
(74) *Attorney, Agent, or Firm*—Oliff & Berridge, PLC

(57) ABSTRACT

A weak light detector (40) which can detect two-dimensional weak radiation at a high speed with high precision. The fluorescence from the DNA chip (46) is incident on a detection part (56) of a detection unit (52). The detection unit (56) has a detection module with a number of detection transistors being placed to correspond to cells of the DNA chip (46). The detection part (56) performs photoelectric conversion of the incident fluorescence (photon) to emit electrons, and amplifies the electrons to make them incident on the detection module. The detection transistors are switched based the Hadamard matrix to operate. A data processing unit (54) reads an output signal of the detection part (56), then performs Hadamard inversion, and determines the detection transistor which outputs the signal.

4 Claims, 9 Drawing Sheets

Fig. 7-a
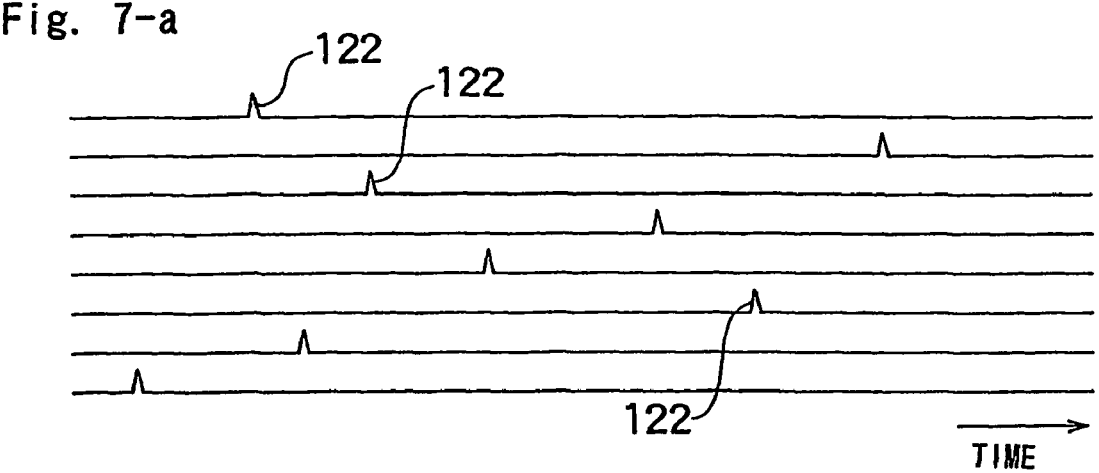
Fig. 7-b
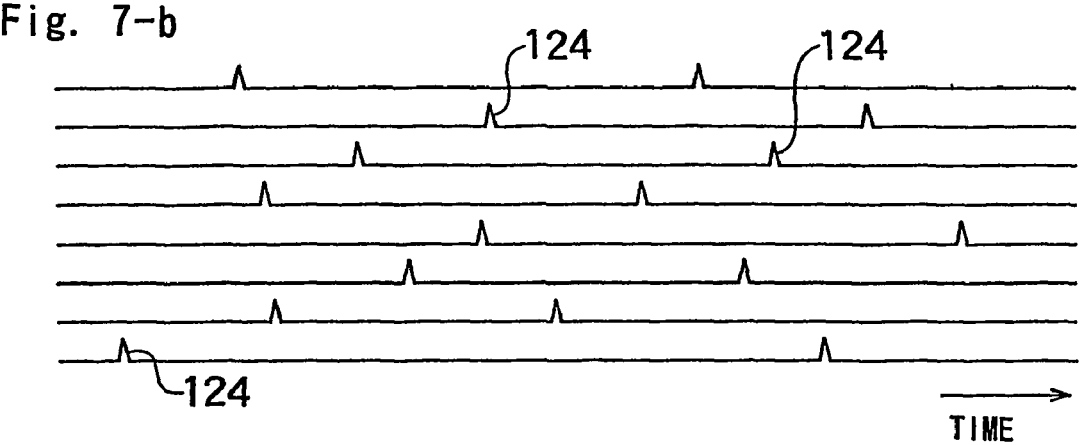
Fig. 7-c

US 7,326,900 B2

TWO-DIMENSIONAL WEAK RADIATION DETECTOR WITH A DETECTION MEANS BASED ON ORTHOGONAL MODULATION

TECHNICAL FIELD

The present invention relates to a two-dimensional weak radiation detector that detects weak electromagnetic waves and corpuscular rays, which are radiated two-dimensionally.

BACKGROUND ART

Recently, much attention is paid to an in situ hybridization by a DNA chip to perform prevention and diagnosis of diseases. This is made by placing a fragment (cells) of a specified site of DNA in a matrix form on a glass base plate. The DNA chip is used in determining whether a tested person has a gene related to a specified disease or not by adding a fluorescent material to a sample such as blood that is extracted from the tested person to label the DNA of the sample, and bringing the sample and the cells on the DNA chip in contact with each other to perform hybridization, and the like.

Conventionally, when it is detected with which cell of the DNA chip the DNA in the sample creates a hybrid, a device called a DNA chip reader as shown in FIG. 11 is used to detect it. The DNA chip reader 10 is a so-called confocal type, and includes a laser light source 14 for irradiating a DNA chip (specimen) 12 placed on an inspection stage not irradiated with laser light. A condenser lens 16 and a pin-hall 18 are placed in series under the laser light source 14 to concentrate a laser beam 21 emitted by the laser light source 14.

The laser beam 21, which passes through the pin-hole 18, is transmitted through a dichroic mirror 22 to separate fluorescence emitted from the DNA chip 12 and the laser beam 21, and thereafter, it is made parallel light by a collimate lens 24. After the laser beam 21, which is made parallel light by the collimate lens 24, is reflected by a pair of galvano mirrors 26 and 28, it is incident on an objective lens 30, and converges on the DNA chip 12 to irradiate to the cells. The galvano mirrors 26 and 28 are for scan-running the laser beam 21 along a surface of the DNA chip 12, and for example, when the galvano mirror 26 is rotated, the laser beam 21 moves in an X-direction on the surface of the DNA chip 12, and when the galvano mirror 28 is rotated, the laser beam 21 moves in a Y-direction. Accordingly, by controlling the rotation of the galvano mirrors 26 and 28, the laser beam 21 can irradiate to optional cells placed in the matrix form on the DNA chip 12.

When the cell of the DNA chip 12 creates a hybrid with the DNA in the sample labeled by the fluorescent material, it emits fluorescence when it is irradiated with the laser beam 21. The fluorescence emitted from this cell is incident on the dichroic mirror 22 via the objective lens 30, the galvano mirrors 28 and 26, and the collimate lens 24. The dichroic mirror 22 selectively deflects only the incident fluorescence at 90 degrees to make it incident on the photoelectron multiplier tube 34 via the pin-hole 32. The photoelectron multiplier tube 34 generates photoelectrons with the incident fluorescence, and amplifies them to output them as a voltage pulse. Accordingly, by monitoring the output of the photoelectron multiplier tube 34, it can be known which cell of the DNA chip 12 emits the fluorescence, that is, it can be known that the gene that creates a hybrid with that cell is included in the sample.

However, the above-described conventional DNA chip reader 10 needs to scan the surface of the DNA chip 12 by moving the laser beam 21 in a step form. For this reason, when the laser beam 21 is scan-moved along the surface of the DNA chip 12 in which N×N of cells are placed in a matrix form, the scanning time is increased exponentially when the number of N increases to 100 to 1000 (the number of cells is ten thousand to a million), and thus tremendous time is required to read the information of the cells. Consequently, there is a trial to place multiple photoelectric multiplier tubes 34 in a plane, irradiate the entire DNA chip 12 with a laser beam, and read output pulse of each of the photoelectric multiplier tubes 34 at once to obtain two-dimensional information, but this is not realistic because the photoelectron multiplier tube 34 is expensive and a large installation space is required.

It is considered to use a CCD type photon counting video camera to obtain the position of the cell, which creates a hybrid of the DNA chip 12 two-dimensionally. The CCD type photon counting video camera performs photoelectric conversion of incident photons to generate photoelectrons, amplifies a photoelectron in the number of electrons in each capillary (channel) by a secondary electron amplification, called a microchannel plate (MCP) constituted by a number of capillaries (capillaries), make them incident on the fluorescent material again to convert the electrons into light, and receive the converted light with the CCD video camera. However, when the CCD type photon counting video camera is used, the following problem arises.

The processing of the photon counting mode is performed for a signal from the CCD video camera. Namely, an output signal of the CCD element, which corresponds to each pixel (pixel) of the CCD video camera is binarized, and the output signals (the number of incident photons) per unit time are counted. However, readout of the output signals for each element of the CCD video camera is no more than about 100 times/s.

On the other hand, the fluorescence occurring from the cells of the DNA chip 12 is extremely weak, and photons are rarely incident on each channel (capillary) of the MCP. In addition, the duration of the pulse of the electrons incident on the CCD element from the MCP is 0.1 to 10 ns, which is exceedingly short. Consequently, each element of the CCD video camera integrates the pulse of the electrons corresponding to the incident photons that rarely come for about 10 ms being a read cycle of the signal, which is $10^6$ to $10^8$ times as long as the pulse duration of the electrons. However, the CCD has a noise called a dark current, this noise is also integrated during the read cycle, and the detection system cannot be realized unless the S/N of the pulse is $10^6$ to $10^8$ or more, which is unpractical.

The present invention is made to eliminate the disadvantages of the aforementioned prior art, and has its object to make it possible to detect two-dimensional weak radiation at a high speed with high precision.

The present invention has another object to make it possible to obtain a two-dimensional color image based on weak radiation with ease.

DISCLOSURE OF THE INVENTION

In order to attain the above-described object, a two-dimensional weak radiation detector according to the present invention is characterized by having a photoelectric conversion part which emits electrons by incidence of photons, an amplification module which is placed to face the photoelectric conversion part, and is provided with a number of electron amplification parts that amplify the electrons emitted by the photoelectric conversion part, a detection module which is provided to correspond to each of the aforementioned electron amplification parts constituting the amplification module, and is provided with a number of electron detection parts on which the electrons from the electron amplification parts are incident, an operation control part which operates each of the aforementioned electron detection parts constituting the detection module based on an orthogonal modulation pattern, and a light incidence position calculation part which obtains positions of the aforementioned photons incident on the aforementioned photoelectric conversion part based on a control signal of the operation control part and an output signal of each of the aforementioned electron detection parts.

Further, a two-dimensional weak radiation detector according to the present invention is characterized by having a photoelectric conversion part which emits electrons by incidence of photons, an amplification module which is placed to face the photoelectric conversion part, and is provided with a number of electron amplification parts that amplify the electrons emitted by the photoelectric conversion part, a detection module which is provided to correspond to each of the aforementioned electron amplification parts constituting the amplification module, and is provided with a number of electron detection parts on which the electrons from the electron amplification parts are incident, an operation control part which operates each of the aforementioned electron detection parts constituting the detection module based on an orthogonal modulation pattern, a light incidence position calculation part which obtains positions of the aforementioned photons incident on the aforementioned photoelectric conversion part, based on a control signal of the operation control part and an output signal of each of the aforementioned electron detection parts, and a wavelength calculation part which obtains energy of the aforementioned photons based on magnitude of the output signal of each of the aforementioned electron detection parts, and converts it into a color signal.

The wavelength calculation part can be constituted to obtain the magnitude of the output signal based on repetition frequency of output pulse signal of the aforementioned electron detection part and convert it into the aforementioned color signal. An emission part, which emits photons by incidence of microwaves or corpuscular rays, may be provided at a front of the photoelectric conversion part.

In the present invention constituted as described above, the photons caused by weak radiation is converted into photoelectrons by the photoelectric conversion part, and after the photoelectrons (electrons) are amplified in number in the amplification module, they are incident on the detection module. The detection module is provided with the electron detection parts corresponding to a number of electron amplification parts of the amplification module, and the electron detection parts are operated according to the orthogonal modulation pattern (for example, the pattern corresponding to each line of the Hadamard matrix being a binary orthogonal modulation pattern). Accordingly, the output signals (data) are always obtained from one fourth of n×n of electron detection parts. Photoelectron incidence position is calculated by inversion (for example, the Hadamart inversion) from the obtained data, and the position of the photons incident on the photoelectric conversion part can be obtained. Accordingly, two-dimensional weak radiation can be two-dimensionally detected at a high speed with high precision, and a two-dimensional screen image by weak radiation can be obtained.

The energy of the incident photon is obtained based on the magnitude of the output signal of the electron detection part, and the output signal is converted into the previously given color signal correspondingly to the energy, whereby when a photon of any wavelengths is inputted, it is possible to make the image of the weak radiation, which is obtained two-dimensionally, a color image, thus making it possible to recognize and understand the state of the two-dimensional weak radiation more easily. Further, color night vision cameras and the like can be easily formed.

If the magnitude of the output signal of the electron detection part is obtained based on the repetition frequency of the output pulse signal, which the electron detection part outputs, an error caused by fluctuations in measurement can be avoided, and the magnitude of the output signal to be detected can be obtained easily and reliably. If the emission part, which emits photons by the incidence of electromagnetic waves or corpuscular rays, is provided at the front of the photoelectric conversion part, weak X-rays and γ-rays, α rays and the like can be detected.

BRIEF DESCRIPTION OF THE DRAWINGS

FIG. 7-*a* is a diagram explaining a state of an output pulse of a data read part according to the embodiment;

FIG. 7-*b* is a diagram explaining a state of the output pulse of the data read part according to the embodiment;

FIG. 7-*c* is a diagram explaining a state of the combined output pulse of the data read part according to the embodiment;

BEST MODE FOR CARRYING OUT THE INVENTION

A preferred embodiment of a two-dimensional weak radiation detector according to the present invention will be explained in detail according to the accompanying drawings.

Figure 1:
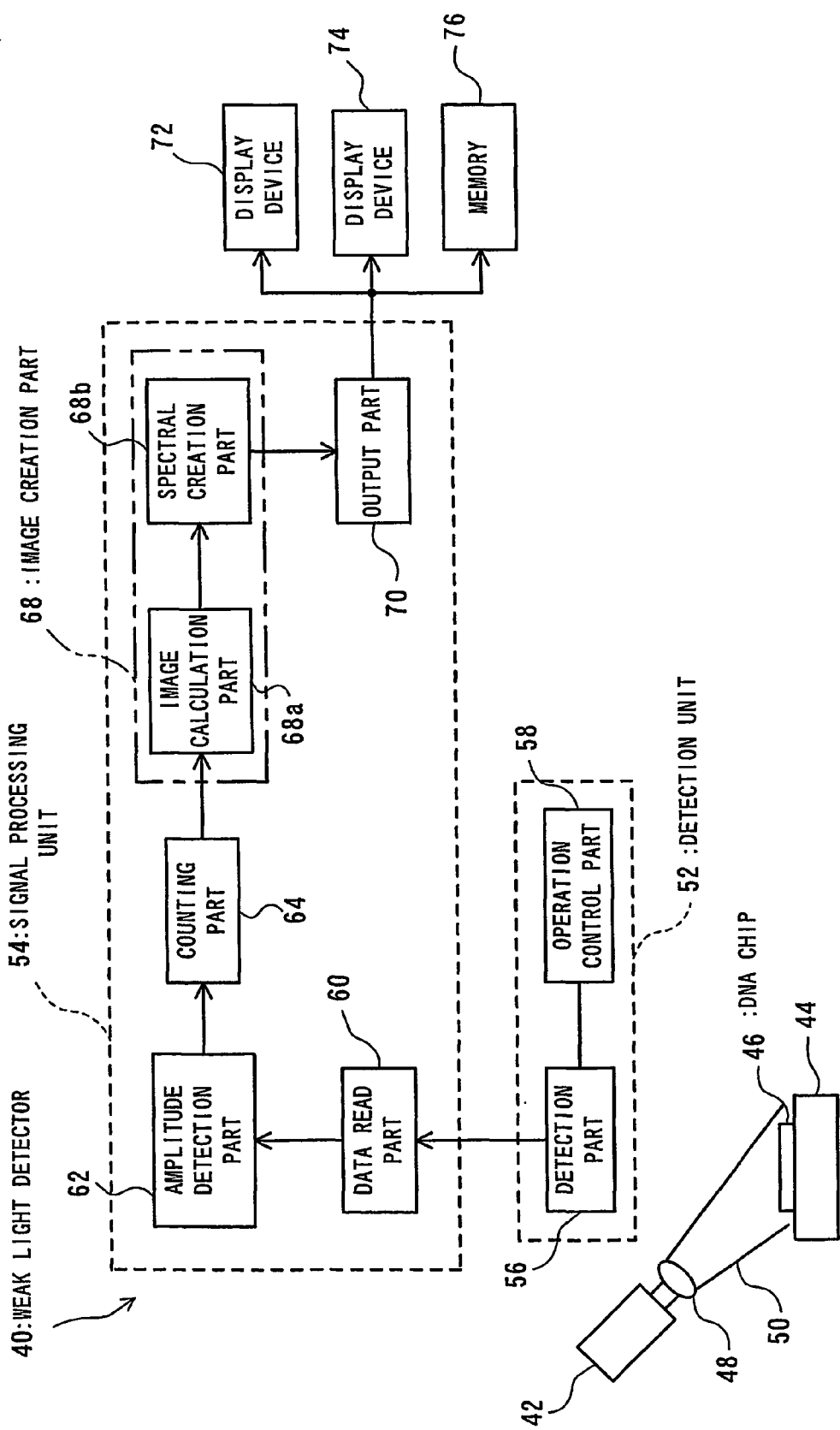
FIG. 1 is a block diagram of a two-dimensional weak radiation detector according to an embodiment of the present invention.

FIG. 1 is a schematic block diagram of the embodiment of the two-dimensional weak radiation detector according to the present invention, and shows an example in which it is applied to a DNA chip reader. In FIG. 1, a weak light detector 40 that is the two-dimensional weak radiation detector has a laser radiation unit 42. The laser radiation unit 42 makes it possible to irradiate a DNA chip 46 to be a specimen, which is placed on an inspection stage 44, with a laser beam 50 via a lens system 48. The weak light detector 40 includes a detection unit 52 placed above the inspection stage 44, and a signal processing unit 54 which obtains positions of cells creating a hybrid, and the like in the DNA chip 46 based on an output signal of the detection unit 52.

The detection unit 52 is constituted by a detecting part 56 including a large number of microcapillaries which detect weak light, and an operation control part 58 which operates the detecting part 56. The signal processing unit 54 has a data read part 60 reading an output signal of the detecting part 56. Further, the signal processing unit 54 has an amplitude detection part 62, which is connected to an output side of the data read part 60, a counting part 64, which is provided at an output side of the amplitude detection part 62, an image creation part 68 into which a signal from the counting part 64 is inputted, and an output part 70, which is provided at an output side of the image creation part 68. The image creation part 68 is formed by an image calculation part 68a and a spectral creation part 68b of which actions will be described later. A display device 74 and a printer 72, which serve as output devices, an external memory 76 and the like are connected to the output part 70.

Figure 2:
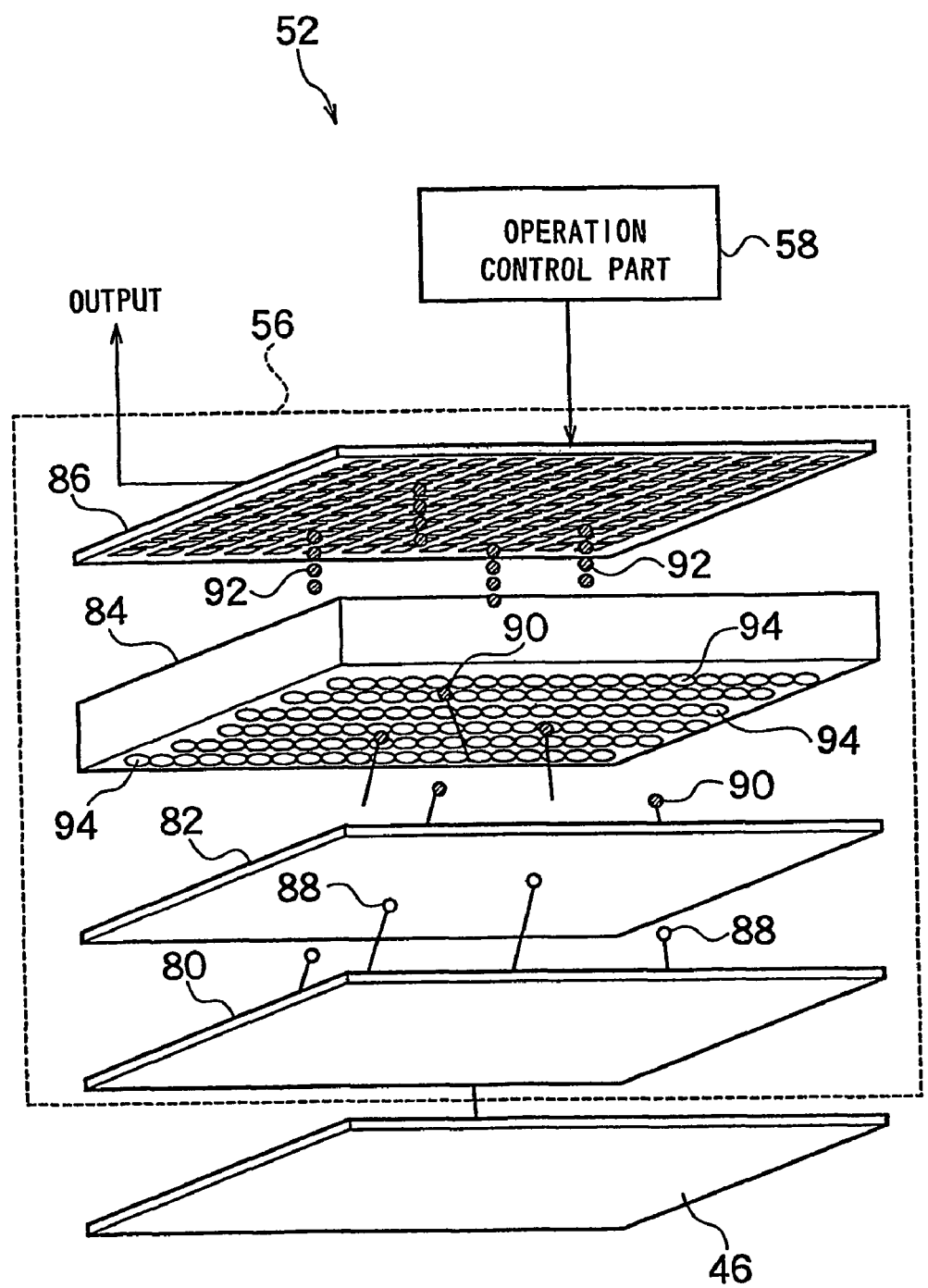
FIG. 2 is an explanatory view of a detail of a detection part according to the embodiment.
Figure 3:
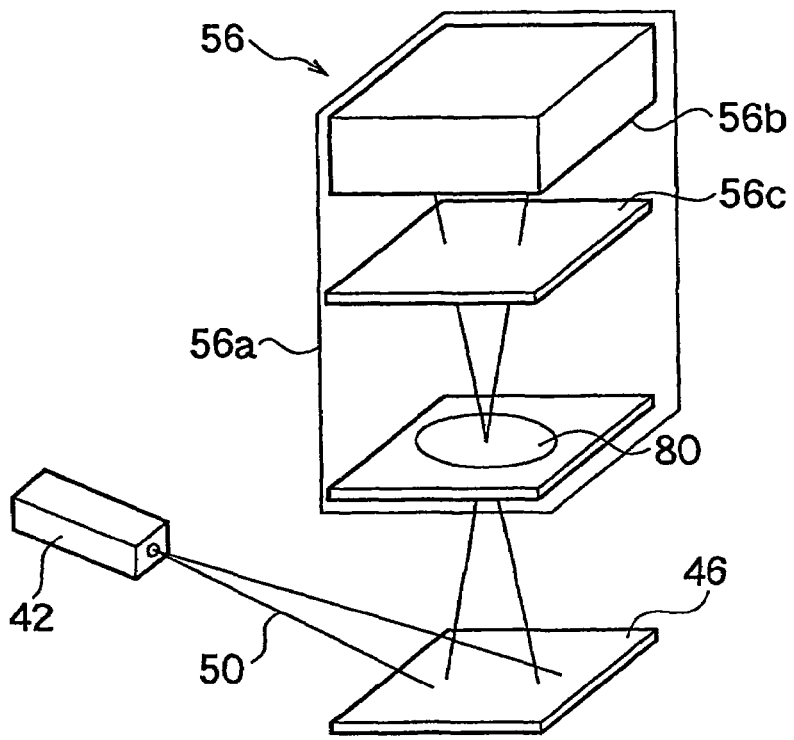
FIG. 3 is a perspective view showing an outline of the detection part according to the embodiment.

The detecting part 56 of the detection unit 52 includes a lens 80, a photoelectric conversion part 82, a microchannel plate 84 to be an amplification module, and a detection module 86 as shown in FIG. 2, and the lens 80 is a detection window. The detection part 56 is provided with a light shielding container 56a which shields the laser beam 50 and extraneous light, and the lens 80 is attached to a front end surface of this light shielding container 56a, as shown in FIG. 3. Further, the photoelectric conversion part 82, the microchannel plate 84, and the detection module 86 are placed behind the lens 80 in this order inside the light shielding container 56a. The photoelectric conversion part 82, the microchannel plate 84, and the detection module 86 constitute an ultra-high speed photon counting type two-dimensional receiver 56b. An optical filter 56c is placed between the lens 80 and the two-dimensional receiver 56b. The optical filter 56c shields a frequency band of laser light and selectively transmits light that is in the frequency band corresponding to fluorescence to allow the light to be incident on the two-dimensional receiver 56b.

Figure 4:
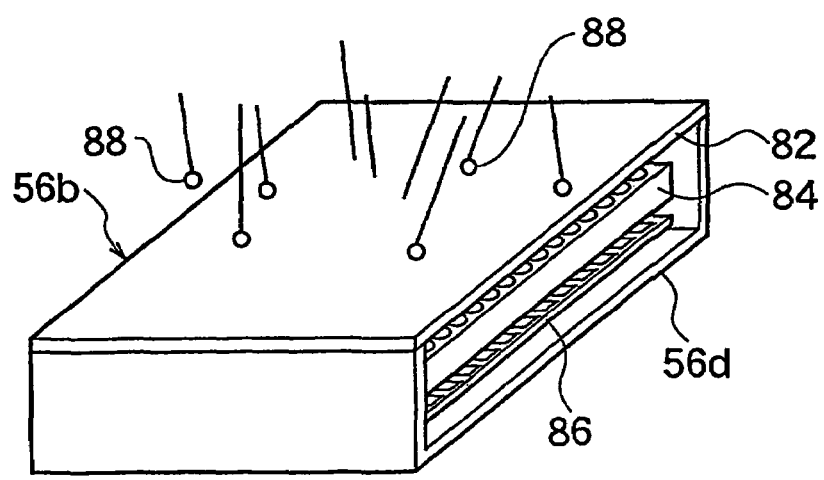
FIG. 4 is a perspective view explaining a two-dimensional receiver constituting the detection part according to the embodiment.

The two-dimensional receiver 56b has a vacuum container 56d as shown in FIG. 4, and the photoelectric conversion part 82 is attached to a back side of a front face of the vacuum container 56d. The microchannerl plate 84 and the detection module 86 are placed inside the vacuum container 56d. In the two-dimensional receiver 56b, the photoelectric conversion part 82, the microchannel plate 84, and the detection module 86 are placed to be in close contact with each other.

The detection part 56 is placed so that the lens 80 faces the DNA chip 46. The lens 80 allows fluorescence which is emitted by the cell of the DNA chip 46 to form an image on the photoelectric conversion part 82. When a fluorescence (photon) 88 transmitted through the lens 80 and the optical filter 56c is incident on the photoelectric conversion part 82, the photoelectric conversion part 82 emits an electron (photoelectron) 90. The electron 90, which the photoelectric conversion part 82 emits, is amplified to be about $10^5$ to $10^7$ times in number in the microchannel plate 84, the detail of which will be described later, to be an amplified electron 92, and is incident on the detection module 86 to be detected by the detection module 86.

Figure 5:
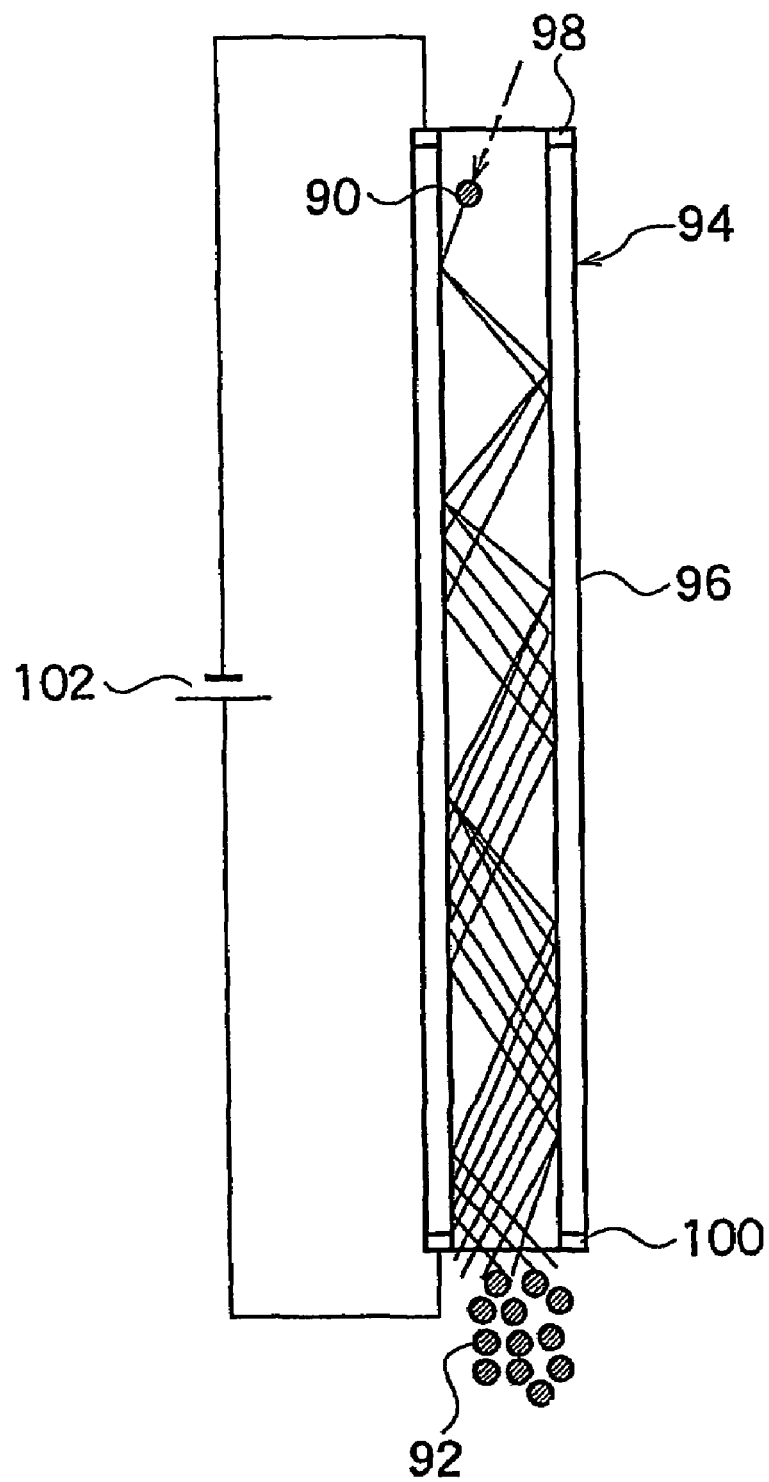
FIG. 5 is an explanatory view of a detail of a microcapillary according to the embodiment.

The microchannel plate 84 has a constitution in which a large number of microcapillaries 94, which are secondary electron multipliers, are placed in a matrix form to face the cells of the DNA chip 46. The microcapillary 94 constituting the microchannel plate 84 is constituted by an accelerating tube 96 with the diameter of 5 μm to 20 μm and the length of about 0.1 mm to 1.0 mm, and a cathode 98 and an anode 100 which are provided at both ends of the accelerating tube 96, as shown in FIG. 5. In the microcapillary 94, the cathode 98 and the anode 100 are connected to a direct-current power supply 102, and a direct-current high voltage of 1000 to 10000V is applied between the cathode 98 and the anode 100. As a result, the electron 90, which is incident on the inside of the accelerating tube 96 from the side of the cathode 98, is accelerated by the high voltage applied between the cathode 98 and the anode 100, and each time the electron 90 collides against an inner wall of the accelerating tube 96, it generates secondary electrons to be amplified to surge in number, which are emitted from the side of the anode 100 as the amplified electrons 92.

Figure 6:
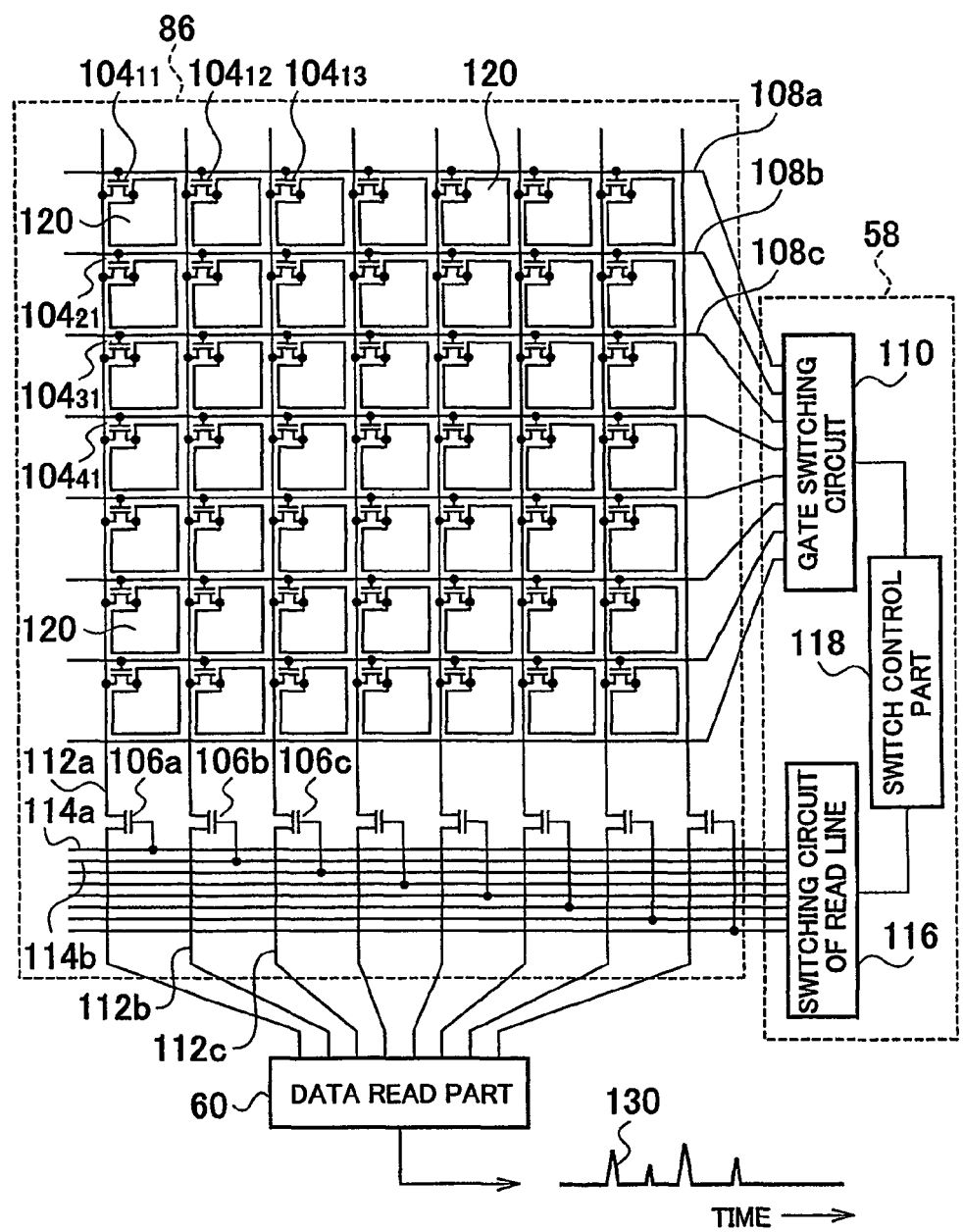
FIG. 6 is an explanatory diagram of a detail of a detection module according to the embodiment.

The detection module 86 is as shown in FIG. 6. Namely, the detection module 86 includes a number of detection transistors 104 ($104_{ij}$) constituted by MOS transistors and a number of read transistors 106 (106a, 106b, 106c . . . ) constituted by the MOS transistors. n×n of the detection transistors $104_{ij}$ (i=1, 2, 3, . . . n, j=1, 2 3, . . . n) are placed in the matrix form corresponding to the microchapillaries 94 constituting the microchannel plate 84. n of the read transistors 106 are provided to correspond to each column of the detection transistors 104 which are placed in the matrix form.

At each line of the detection transistors 104, gates are connected to a gate control line 108 (108a, 108b, 108c, . . . ), and these gate control lines 108 are connected to a gate switching circuit 110 constituting the operation control part 58. At each column of the detection transistors 104, drains are connected to a source of the read transistor 106 via a data line 112 (112a, 112b, 112c, . . . ). At each of the read transistors 106, a drain is connected to the data read part 60 of the signal processing unit 54, and each gate is connected to a corresponding read line 114 (114a, 114b, 114c, . . . ). Detection electrodes 120 provided to face an output side of the microcapillary 94 are connected to sources of the detection transistors 104.

Each of the read lines 114 is connected to a read line switching circuit 116 constituting the operation control part 58. The operation control part 58 is constituted by the gate switching circuit 110, the read line switching circuit 116, a switching control part 118 and the like. The switching control part 118 generates a switching control signal based on a binary orthogonal modulation pattern as the detail will be described later, and it gives the switching control signal to the gate switching circuit 110 and the read line switching circuit 116, so that each of the detection transistors 104 and each of the read transistors 106 are switched to operate based on the orthogonal modulation pattern.

An operation of the weak light detector 40 according to the embodiment which is constituted as above is as follows. First, the DNA chip 46 which creates a hybrid with a sample not shown is placed on the inspection stage 44, and the entire DNA chip 46 is irradiated with the laser beam 50 by the laser radiation unit 42. If the cell of the DNA chip 46 creates a hybrid with the DNA of the sample labeled with a fluorescent material, the cell emits fluorescence. This fluorescence (photon) is incident on the detection part 56 of the detection unit 52 provided above the inspection stage 44.

The photon 88 which is incident on the detection part 56 is transmitted through the lens 80 and converted into an electron (photoelectron) 90 by the photoelectric conversion part 82, as shown in FIG. 2. The electron 90 is incident on the amplifying tube 96 of the microcapillary 94 constituting the microchannel plate 84 (see FIG. 5). When the electron 90 enters the amplifying tube 96, it is accelerated by a high direct current voltage applied at both ends of the amplifying tube 96, then collides against the inner wall of the accelerator tube 96 many times to generate the secondary electrons, and the number of it is amplified by about $10^5$ to $10^7$ times. The amplified electrons 92 are incident on the detection electrodes 120 of the detection module 86 and electrically charge the detection electrodes 120. Accordingly, the detection transistors 104 are successively switched to operate, whereby it is known which detection transistors 104 have the detection electrodes 120 that the amplified electrons 92 are incident on.

Incidentally, the fluorescence emitted by the cell of the DNA chip 46 is extremely weak, and the electron 90 generated by the photoelectric conversion is only rarely incident on each of the microcapillaries of the micro channel plate 84. Namely, the amplified electrons 92 are only rarely incident on each of the detection electrodes 120 of the detection module 86. Consequently, when data is read out by selecting one gate channel (one gate control line 108) and one read channel (one read control line 114), the data read part 60 outputs a detection pulse 122 only sparsely. In addition, since the gate control line 108 and the read control line 114 are successively switched, n×n times of switching are required, and if the number of n is 100 to 1000 (the number of cells is ten thousands to one million), tremendous reading time is required.

Thus, when a number of gate control lines 108 and one of the read control lines 114 are selected and a number of detection transistors 104 are driven at the same time, more pulses 124 than when the detection transistors 104 are individually driven can be obtained for each of the data lines 112 as shown in FIG. 7-b. When the data read part 60 outputs a pulse train which is formed by combining signals of a number of read lines, the density of the detection pulse 122 in time sequence can be made high, as shown in FIG. 7-c. However, if things continue the way they are, it cannot be known which detection transistor 104 provides the detection pulse 122, and therefore a two-dimensional image of the photon emission cannot be obtained, thus making it impossible to determine which cell of the DNA chip 46 creates the hybrid. Consequently, in this embodiment, a driving signal based on the orthogonal modulation pattern is generated and thereby the detection transistor 104 is driven.

As the orthogonal modulation pattern described above, a modulation pattern corresponding to each line of a Hadamard matrix, which is a binary orthogonal modulation pattern, is suitable. The Hadamard matrix is constituted by elements of "+1" and "−1", and is a symmetric matrix in which the elements at the symmetrical positions along the diagonal line are the same. For example, when a first order Hadamard matrix $H^{(1)}$ is written in concrete, it is as follows.

$$H^{(1)} = \begin{bmatrix} 1 & 1 \\ 1 & -1 \end{bmatrix} \quad \text{[Formula 1]}$$

A second order and third order Hadamard matrixes $H^{(2)}$ and $H^{(3)}$ can be written as formula 2 and formula 3.

$$H^{(2)} = \begin{bmatrix} 1 & 1 & 1 & 1 \\ 1 & -1 & 1 & -1 \\ 1 & 1 & -1 & -1 \\ 1 & -1 & -1 & 1 \end{bmatrix} \quad \text{[Formula 2]}$$

$$H^{(3)} = \begin{bmatrix} 1 & 1 & 1 & 1 & 1 & 1 & 1 & 1 \\ 1 & -1 & 1 & -1 & 1 & -1 & 1 & -1 \\ 1 & 1 & -1 & -1 & 1 & 1 & -1 & -1 \\ 1 & -1 & -1 & 1 & 1 & -1 & -1 & 1 \\ 1 & 1 & 1 & 1 & -1 & -1 & -1 & -1 \\ 1 & -1 & 1 & -1 & -1 & 1 & -1 & 1 \\ 1 & 1 & -1 & -1 & -1 & -1 & 1 & 1 \\ 1 & -1 & -1 & 1 & -1 & 1 & 1 & -1 \end{bmatrix} \quad \text{[Formula 3]}$$

Namely, the Hadamard matrix can be defined by the following recurrence formula.

$$H^{(0)} = 1, \, H^{(k)} = \begin{bmatrix} H^{(k-1)} & H^{(k-1)} \\ H^{(k-1)} & -H^{(k-1)} \end{bmatrix} \quad \text{[Formula 4]}$$

It should be noted that in formula 4, k represents the degree.

Figure 8:
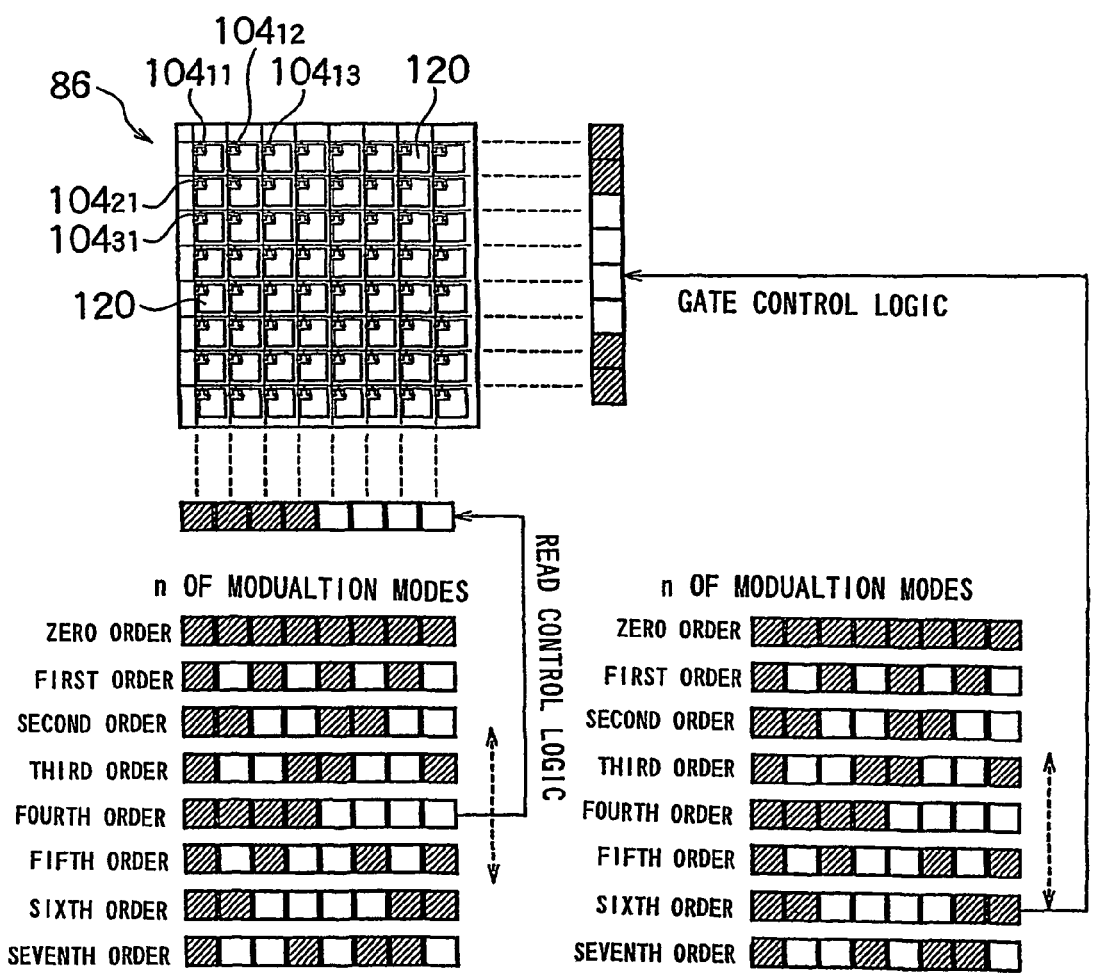
FIG. 8 is an explanatory diagram of a method for controlling an operation of a detection module according to the embodiment.

Thus, in the embodiment, the switching control part 118, which constitutes the operation control part 58 of the detection unit 52, creates a switching operation signal for the detection transistor 104 based on the Hadamard matrix which corresponds to "+1" of the case in which the switch is turned on, and "−1" of the case in which the switch is turned off, and the switching control part 118 gives it to the gate switching circuit 110 and the read line switching circuit 116 as a switching control signal. For example, when the detection module 86 is constituted by 8×8 of the detection transistors 104, the operation signal for the detection transistors 104 is as shown in FIG. 8. The diagonally shaded areas correspond to +1 which is turned on by being given the operation voltage, and the open areas correspond to −1 which is turned off.

Namely, the switching control part 118 gives the switching control signal according to the Hadamard matrix to the gate switching circuit 110, then it applies the gate voltage to the gate of each of the detection transistors 104 via the gate control line 108 by switching the gate voltage according to the Hadamard matrix, and gives the switching signal based on the Hadamard matrix to the read line switching circuit 116 to switch the read transistors 106 according to the Hadamard matrix to operate them. For example, when the number of the detection transistors 104 is 8×8, the switching control part 118 creates 8 modulation modes shown in the lower part of FIG. 8 based on the Hadamard matrix, first gives the operation signal of zero order (switching signal) shown in the right side of the lower part of FIG. 8 to the gate switching circuit 110, connects all the gate control lines 108 to a gate power supply, applies gate voltage to the gates of all the detection transistors 104, gives the switching signals of zero order to the seventh order in the left side of the lower part of FIG. 8 to the read line switching circuit 116, and by doing so successively switches the read transistors 106 based on the Hadamard matrix to drive them.

When switching of the 0 order to the seventh order is finished for the read transistors 106, the switching control part 118 gives the drive signal of the first order to the gate switching circuit 110, and applies voltage to the gates of the detection transistors 104 connected to the gate control line 108*a* in the first, the third, the fifth and the seventh lines, in which state the transistors 106 are switched to the zero order to the seventh order. In this manner, the switching control part 118 switches the read transistors 106 from the zero order to the seventh order each time it switches the voltage which is applied to the gates of the detection transistors 104 from the zero order to the seventh order. As a result, the gate voltage is always applied to a half of the detection transistors 104, a half of the data lines 112 are on, and the output signals are inputted into the data read part 60 from an one forth of the total number of the detection transistors 104.

The data read part 60 converts currents, which are inputted as the output signals of the detection transistors 104, into voltage to amplify them, and outputs the output pulse 130 as shown in FIG. 6 as voltage. The output pulse 130 is inputted into the amplitude detection part 62 of the signal processing unit 54 as shown in FIG. 1. The output pulse 130 of the data read part 60 may be subjected to A/D conversion.

When the gates of the detection transistors 104 are switched based on the Hadamard matrix and voltage is applied to them and the read transistors 106 are switched according to the Hadamard matrix to operate them, demodulation is performed with use of the Hadamard inversion from the pulse 130 (data modulated based on the Hadamard matrix) outputted by the data read part 60, whereby the detection transistor 104 which outputs the pulse 130 can be obtained. Namely, when the pulse repetition frequency data matrix with the gate control line 108 as a row and with the read control line 114 (data line 112) as a column is considered, the Hadamard inversion (two-dimensional Hadamard inversion) is performed in the row direction and the column direction, whereby pulse repetition frequency of the detection transistor 104 by the combination of one of the gate control lines 108 and one of the read control lines 114, which are optionally selected, can be determined. Accordingly, the image calculation part 68*a* is an incident position calculating part as the detail will be described later, and the Hamadard inversion is performed based on the data of the counting part 64, whereby the detection transistor 104 on which the amplified electron 92 is incident can be obtained, the microcapillary 94 into which the photoelectron 90 is inputted can be determined, and it can be known which position of the photoelectric conversion part 82 the photon 88 is incident on. Consequently, it can be known which cell of the DNA 46 emits the fluorescence.

Figure 9:
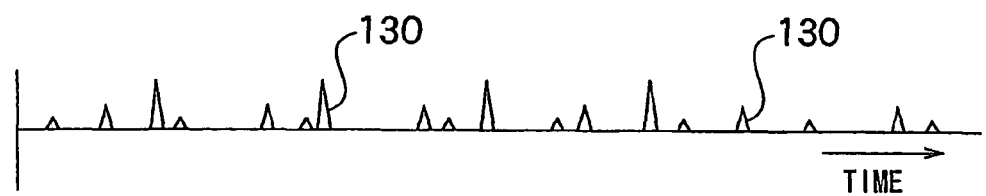
FIG. 9 is an explanatory diagram of the output pulse, which the data read part according to the embodiment outputs.

The amplitude detection part 62 of the signal processing unit 54 obtains the amplitude (magnitude of voltage) of the pulse 130 outputted by the data read part 60 and inputs it into the counting part 64. Namely, when a number of fluorescent materials are added to the sample not shown to be combined with the cells of the DNA chip 46, a number of fluorescences are emitted from the DNA chip 46 when the cells create hybrids. Accordingly, if the fluorescent materials differ, the fluorescences with different wavelengths are emitted, and the energies of the photons 88 incident on the photoelectric conversion part 82 differ respectively. As a result, the electrons (photoelectrons) 90 generated in the photoelectric conversion part 82 differ in kinetic energy due to difference in the energy of the incident photons 88, and when the fluorescence with a short wavelength is incident, the electron 90 with a large kinetic energy is generated. When the electron 90 with a larger kinetic energy is incident on the microcapillary 94, more secondary electrons are generated, and the number of the amplified electrons 92 becomes larger. Accordingly, the output of the detection transistor 104 corresponding to the microcapillary 94, on which the electron 90 based on the photon 88 by the fluorescence with a short wavelength is incident, becomes larger, and the amplitude of the pulse 130 (height of the pulse 130) outputted by the date read part 60 becomes larger. Namely, the output pulses 130 of the data read part 60 have different amplitudes as shown in FIG. 9 when the DNA chip 46 emits a number of fluorescences.

The counting part 64 reads the output signal of the amplitude detection part 62 in synchronism with the switching control part 118 of the operation control part 58 outputting a switching control signal to the read line switching circuit 116, counts the pulses 130 outputted by the data read part 60 for each amplitude obtained by the amplitude detection part 62, and inputs it into the image calculation part 68*a* of the image creation part 68. The image calculation part 68*a* that is the incident position calculation part stores the counting value outputted by the counting part 64 in an internal memory not shown for each magnitude of the pulses 130 correspondingly to the readout mode of the data. When the readout of the data according to the modulation mode based on the Hadamard matrix is finished, the image calculation part 68*a* reads the counting value from the counting part 64, which is stored in the internal memory, and performs Hadamard inversion of this data according to the computing equation which is given in advance. Consequently, as described above, the image calculation part 68*a* obtains the position of the detection transistor 104 which outputs the signal, namely, the position of the microcapillary 94 on which the electron (photoelectron) 90 is incident, determines the cells inside the DNA chip 46, which emit the fluorescence, and obtains pulse repetition frequency as to the magnitude of the output pulse 130 (magnitude of the amplitude) of the data read part 60 for each cell.

Figure 10:
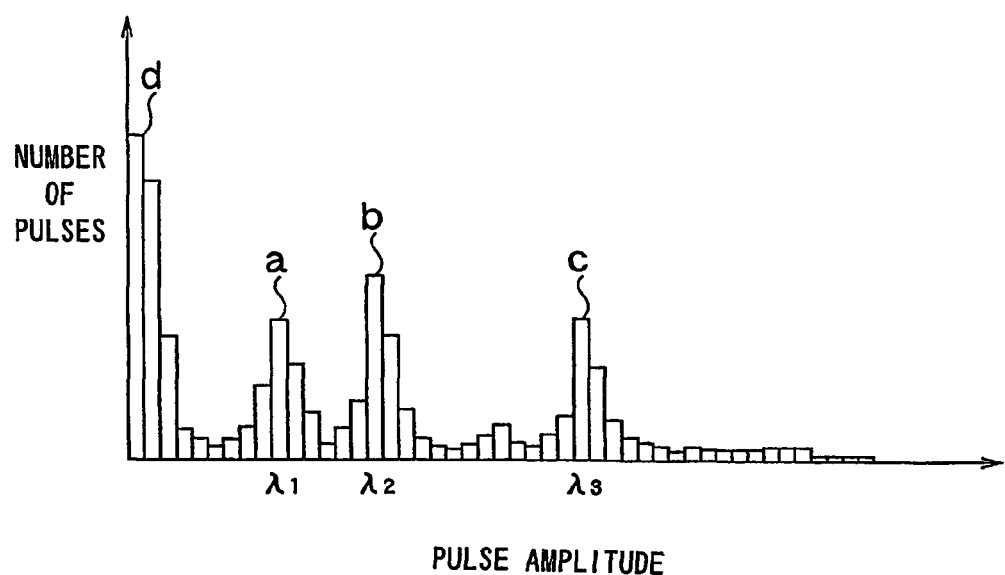
FIG. 10 is an explanatory diagram of an energy spectral based on the output pulse of the data read part according to the embodiment.
Figure 11:
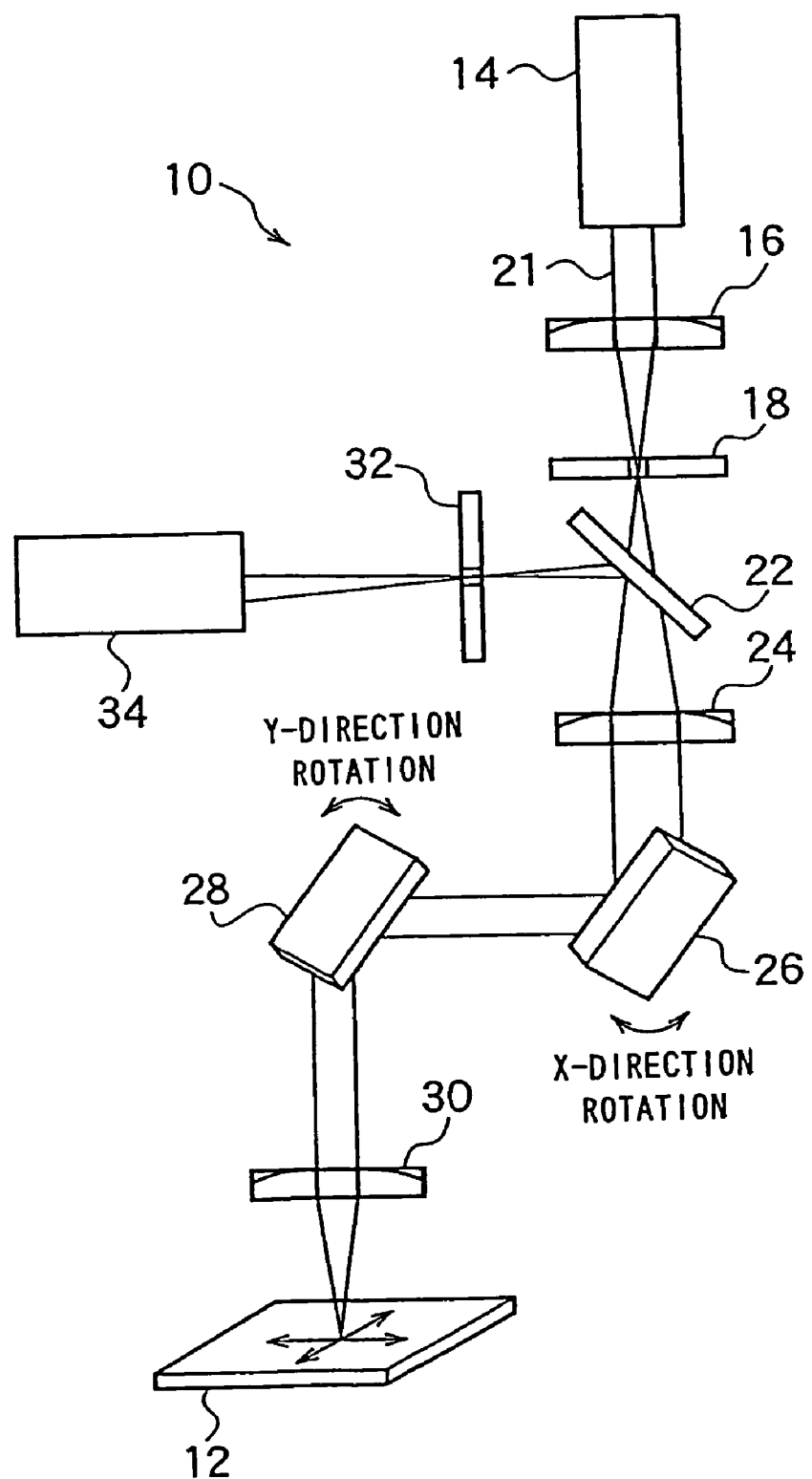
FIG. 11 is an explanatory view of a conventional DNA chip reader.

The spectral creation part 68*b* constituting the image creation part 68 reads the pulse repetition frequency (number of pulses) for each amplitude of the output pulses 130 obtained by the image calculation part 68*a*, and creates an energy spectral in respect of the output pulse 130 for each pixel as shown in FIG. 10. Further, the spectral creation part 68*b* obtains the energy (wavelength of fluorescence) of the photon which is incident on the detection unit 52 based on the created energy spectral. Namely, the spectral creation part 68*b* obtains wavelengths $\lambda_1$, $\lambda_2$ and $\lambda_3$ of the fluorescence corresponding to maximum values a, b and c of the pulse repetition frequencies in FIG. 10 from the functional relationship between the wavelength of the fluorescence and the amplitude of the output pulse 130 of the data read part 60, and it selects the color which is given in advance to the wavelength $\lambda$ to convert it into a color signal. In this situation, the wavelength conversion part 68*b* changes the depth of the color (magnitude of the color signal) according to the number (frequency) of the pulses in FIG. 10. The color signal which is outputted by the spectral creation part 68*b* is outputted to the display device 72 and the like via the output part 70. As a result, the cells creating the hybrids of the DNA chip 46 are displayed as ordinary two-dimensional color images. Consequently, weak radiation of fluorescence or the like which is two-dimensionally emitted can be detected at a high speed with high precision, and a two-dimensional image by weak radiation can be obtained. A peak d corresponding to the area with the wavelength $\lambda$ of zero corresponds to a noise.

In the aforementioned embodiment, the explanation is made about the case in which the detection part 56 is constituted by the lens 80, the photoelectric conversion part 82, the microchannel plate 84, and the detection module 86, but an emission part such as a scintillator may be provided at the front of the lens 80. By providing the emission part like this, very weak electromagnetic waves and corpuscular rays, such as X-rays, γ-rays, electron rays and α-rays can be two-dimensionally detected and visualized.

The embodiment explained above is the explanation of one mode of the present invention, and the present invention is not limited to this. For example, in the aforementioned embodiment, the explanation is made about the case in which the present invention is applied to the detection of the cells creating hybrids of the DNA chip 46, but it can be used as a color night vision camera.

As explained thus far, according to the present invention, a number of electron detection parts constituting the detection module are operated according to the orthogonal modulation pattern (for example, the pattern corresponding to each line of the Hadamard matrix), then the output signals (data) are always obtained from one fourth of n×n of electron detection parts, and inversion of the data is performed with respect to the obtained output signals in the incident position calculation part, whereby the electron detection parts which output the output signals can be determined, and the position of the photons incident on the photoelectric conversion part can be obtained. Accordingly, two-dimensional weak radiation can be two-dimensionally detected at a high speed with high precision, and a two-dimensional visual image by weak radiation can be obtained.

In the present invention, the energy of the incident photon is obtained based on the magnitude of the output signal of the electron detection part, and the output signal is converted into the color signal, which is given in advance, correspondingly to the energy, and therefore it is possible to make the image of the weak radiation, which is obtained two-dimensionally, a color image, when photons based on light with a number of wavelengths are inputted, thus making it possible to recognize and understand the state of the two-dimensional weak radiation more easily.

In the present invention, the magnitude of the output signal of the electron detection part is obtained based on the frequency of the output signal which the electron detection part outputs, thus making it possible to avoid an error caused by fluctuations in measurement and obtain the magnitude of the output signal to be detected easily and reliably. Since the emission part, which emits photons by the incidence of electromagnetic waves or corpuscular rays, is provided at the front of the photoelectric conversion part, it is possible to detect weak X-rays and γ-rays, α rays and the like.

INDUSTRIAL AVAILABILITY

The present invention can be utilized for a two-dimensional weak radiation detector which detects weak microwaves and corpuscular rays, which are two-dimensionally radiated.

The invention claimed is:
1. A two-dimensional weak radiation detector, comprising:
   a photoelectric conversion part which emits electrons by incidence of photons;
   an amplification module which is placed to face the photoelectric conversion part, and is provided with a number of electron amplification parts that amplify the electrons emitted by the photoelectric conversion part;
   a detection module which is provided to correspond to each of said electron amplification parts constituting the amplification module, and is provided with a number of electron detection parts on which electrons from the electron amplification parts are incident;
   an operation control part which operates each of said electron detection parts constituting the detection module based on an orthogonal modulation pattern;
   a data read part which combines signals detected by a number of electron detection parts operated by said operation control part based on an orthogonal modulation pattern in time sequence and outputs the combined signals; and
   a light incidence position calculation part which obtains positions of said photons incident on said photoelectric conversion part, based on a control signal of the operation control part and an output signal of each of said electron detection parts.

2. A two-dimensional weak radiation detector, comprising:
   a photoelectric conversion part which emits electrons by incidence of photons;
   an amplification module which is placed to face the photoelectric conversion part, and is provided with a number of electron amplification parts that amplify the electrons emitted by the photoelectric conversion part;
   a detection module which is provided to correspond to each of said electron amplification parts constituting the amplification module, and is provided with a number of electron detection parts on which electrons from the electron amplification parts are incident;
   an operation control part which operates each of said electron detection parts constituting the detection module based on an orthogonal modulation pattern;
   a data read part which combines signals detected by a number of electron detection parts operated by said operation control part based on an orthogonal modulation pattern in time sequence and outputs the combined signals;
   a light incidence position calculation part which obtains positions of said photons incident on said photoelectric conversion part, based on a control signal of the operation control part and an output signal of each of said electron detection parts; and
   a wavelength calculation part which obtains energy of said photons based on a magnitude of the output signal of each of said electron detection parts, and converts the magnitude into a color signal.

3. The two-dimensional weak radiation detector according to claim 2,
   wherein said wavelength calculation part obtains the magnitude of the output signal based on output pulse repetition frequency of the output signal of said electron detection part and converts the output pulse repetition frequency into said color signal.

4. The two-dimensional weak radiation detector according to claim 1,
   wherein an emission part, which emits the photons by incidence of microwaves or corpuscular rays, is provided at a front of said photoelectric conversion part.

* * * * *